(12) United States Patent
Homann

(10) Patent No.: US 10,932,740 B2
(45) Date of Patent: Mar. 2, 2021

(54) OPTIMIZATION OF X-RAY IMAGING DURING MAMMOGRAPHIC EXAMINATION

(71) Applicant: KONINKLIJKE PHILIPS N.V., Eindhoven (NL)

(72) Inventor: Hanno Heyke Homann, Hannover (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 898 days.

(21) Appl. No.: 15/028,736

(22) PCT Filed: Oct. 21, 2014

(86) PCT No.: PCT/EP2014/072489
§ 371 (c)(1),
(2) Date: Apr. 12, 2016

(87) PCT Pub. No.: WO2015/062903
PCT Pub. Date: May 7, 2015

(65) Prior Publication Data
US 2016/0235379 A1    Aug. 18, 2016

(30) Foreign Application Priority Data
Oct. 30, 2013   (EP) .................................... 13190865

(51) Int. Cl.
*A61B 6/00* (2006.01)
*A61B 5/00* (2006.01)

(52) U.S. Cl.
CPC ............ *A61B 6/502* (2013.01); *A61B 5/0053* (2013.01); *A61B 5/708* (2013.01); *A61B 6/5217* (2013.01); *A61B 6/542* (2013.01)

(58) Field of Classification Search
CPC ........... A61B 6/00; A61B 6/04; A61B 6/0407; A61B 6/0414; A61B 6/0492; A61B 6/502;
(Continued)

(56) References Cited

U.S. PATENT DOCUMENTS

2004/0141588 A1   7/2004   Francke
2007/0249925 A1   10/2007  Hoheisel
(Continued)

FOREIGN PATENT DOCUMENTS

JP    2008142343 A    6/2008
WO    2013/076622     5/2013

OTHER PUBLICATIONS

Wellman, et al., "Breast Tissue Stiffness in Compression is Correlated to Histological Diagnosis", Harvard Bio-Robotics Laboratory Technical Report (1999). (http://biorobotics.harvard.edu/pubs/1999/mechprops.pdf).

(Continued)

*Primary Examiner* — Anastasia Midkiff
(74) *Attorney, Agent, or Firm* — Larry Liberchuk

(57) ABSTRACT

A method for optimizing an X-ray imaging system during a mammographic examination. In order to provide an optimization of the X-ray imaging a breast is compressed between a support plate and a compression plate. A force-height curve is then acquired during the compression. An elasticity value of the breast is determined based on the force-height curve. A parameter of the X-ray imaging system is optimized based on the determined elasticity value.

11 Claims, 4 Drawing Sheets

(58) Field of Classification Search
CPC ......... A61B 6/5294; A61B 6/54; A61B 6/542;
A61B 6/544; A61B 6/545; A61B
2560/00; A61B 2560/02; A61B
2560/0223; A61B 2560/0266; A61B
2560/04; A61B 2560/0462; A61B
2560/06; A61B 2562/0247; A61B
2562/0252; G01B 5/00; G01B 5/02;
G01B 5/06; G01B 5/061; G01B 5/30;
G01B 7/02; G01B 7/06; G01B 7/14;
G01B 11/00; G01B 11/02; G01B 11/06;
G01B 11/14; G01B 11/16; G01B 21/00;
G01B 21/02; G01B 21/08; G01B 21/32;
A61H 2201/5058; A61H 2201/5061;
A61H 2201/5071; A61H 2205/00; A61H
2205/08; A61H 2205/082
See application file for complete search history.

(56) References Cited

U.S. PATENT DOCUMENTS

| | | | |
|---|---|---|---|
| 2010/0054401 A1* | 3/2010 | Blendl | A61B 6/4233 |
| | | | 378/37 |
| 2014/0093034 A1* | 4/2014 | Takata | A61B 6/544 |
| | | | 378/37 |
| 2014/0328458 A1 | 11/2014 | Erhard | |

OTHER PUBLICATIONS

Poulos, et al., "The application of breast compression in mammography: a new perspective", Radiography 10, pp. 131-137 (2004).

* cited by examiner

OPTIMIZATION OF X-RAY IMAGING DURING MAMMOGRAPHIC EXAMINATION

CROSS REFERENCE TO RELATED APPLICATIONS

This application is the U.S. National Phase application under 35 U.S.C. § 371 of International Application No. PCT/EP2014/072489, filed Oct. 21, 2014, published as WO 2015/062903 on May 7, 2015, which claims the benefit of European Patent Application Number 13190865.9 filed Oct. 30, 2013. These applications are hereby incorporated by reference herein.

FIELD OF THE INVENTION

The present invention relates to mammography. In particular, the present invention relates to a method and a corresponding system for optimizing X-ray imaging during a mammographic examination. Furthermore, the present invention relates to a computer program element and a computer readable medium.

BACKGROUND OF THE INVENTION

Mammography imaging is used for example for breast cancer screening. During mammography a breast under examination is mechanically compressed and subsequently a radiographic image of the flattened breast tissue is acquired. The mechanical compression of the breast prevents motion artefacts in the images. Moreover, the compression helps to obtain a more homogeneous breast tissue thickness and hence reduces the average X-ray dose. Compression techniques are for example known from WO 2013/076 622 A1.

Therein, the female breast is mostly composed of two tissue types: glandular tissue and fatty tissue. A measure of glandular tissue volume fraction in the breast is denoted as glandularity (g). Usually the glandularity may be estimated after acquisition of X-ray mammography images and is clinically important for cancer risk assessment.

The glandularity value may also be measured prior to X-ray imaging by way of a pre-scan. This value may be used to adjust the settings of the following mammography, as the X-ray attenuation on the path through the breast depends on the glandularity value.

However, a pre-scan may prolong the overall examination time and thus the time of compression of the breast which implies additional discomfort for the patient. Furthermore, a pre-scan may cause a higher dose for the patient.

SUMMARY OF THE INVENTION

Thus, there may be a need to provide a method and a system which provides a possibility to enhance the X-ray imaging during mammographic examination without causing additional discomfort or additional dose for the patient.

The object of the present invention is solved by the subject-matter of the independent claims. Further exemplary embodiments are evident from the dependent claims and the following description.

According to a first aspect of the present invention a method for optimizing X-ray imaging during a mammographic examination is provided, the method comprises the following steps: compressing a breast between a support plate and a compression plate; acquiring a force-height curve during compression; radiation-free determination of an elasticity value of the breast based on the force-height curve; and optimizing a parameter of an X-ray imaging system based on the determined elasticity value.

In other words the idea of the invention may be seen in providing a prediction or estimation of the elasticity value of a breast by measuring elasto-mechanical properties of the breast. For this purpose, a breast under examination is compressed e.g. between two planar paddles and the pressure force (F) and the height (L) of the breast over time are recorded. From the recorded force-height curve a density or elasticity of the breast may be calculated. Using a model of the elasto-mechanical properties of the breast the elasticity value may be derived from the force-height curve. Therein, the model may be based on a set of equations or on a database of measured values. Furthermore, the elasticity value is advantageously employed to individually adjust the settings of the X-ray system to the breast under examination. Therein, the elasticity value represents the stiffness, the elasticity or the glandularity (g) of the breast under examination.

By determining the elasticity value and particularly the glandularity value based on the force-height curve a radiation-free assessment of the clinically important value is provided. I.e. a pre-scan may be avoided. Thus, as compared to a determination of the glandularity by way of an X-ray pre-scan, the overall dose during the mammographic examination may be reduced. Furthermore, the overall duration of the mammographic examination and also the compression time, which may involve pain for the patient, may be reduced.

Moreover, the image quality of the mammographic examination is enhanced because the parameters of the X-ray scan are individually optimized to the breast under examination. As the elasticity and particularly the glandularity value of a breast may heavily influence the attenuation of X-rays, the personalized setting of the parameters of the X-ray imaging system greatly enhances the image quality.

Additionally, based on the determined elasticity value or glandularity, the compression force during the X-ray scan may be adjusted. For example, for breasts with a lot of fatty tissue the pressure force may be reduced, while for breasts with a high glandular tissue volume fraction the force may be increased e.g. in agreement with the person under examination. Furthermore, in certain cases where the density of the breast is very high, i.e. the glandularity is very high, an output signal may indicate that a magnetic resonance (MRI) and/or an ultrasound examination may be a sensible alternative.

According to an exemplary embodiment of the invention the optimized parameter of the X-ray system is at least one parameter of the following group of parameters: a tube anode voltage of an X-ray source, a tube current of the X-ray source, an X-ray exposure time, X-ray pre-filter properties such as an X-ray pre-filter material or pre-filter thickness, and at least one X-ray detector energy threshold value. The optimization of these parameters may help in enhancing the signal to noise ratio (SNR), in enhancing the image contrast and possibly in reducing exposure time.

According to a further exemplary embodiment of the invention the elasticity value is determined automatically.

According to a further exemplary embodiment of the invention the method further comprises providing a first output signal representative of the elasticity value. Therein, the first output signal may be an optical and/or an acoustical signal.

According to a further exemplary embodiment of the invention the method further comprises: determining a compression force limit based on at least one of the following quantities: the breast contact area, the stiffness of the breast and the glandularity of the breast; providing a second output signal representative of the relation between the quantity and the compression force limit. Therein, the second output signal is provided when the compression force limit is reached during the mammographic examination.

According to a second aspect of the present invention a system for optimizing X-ray imaging during a mammographic examination is provided. The system comprises an X-ray imaging system for acquiring radiographic images of the breast, a support plate for supporting a breast while radiographic images are obtained; a compression plate for compressing the breast between the support plate and the compression plate while the radiographic images are obtained; a monitoring unit for acquiring a force-height curve during compression; and a processing unit for radiation-free determination of the elasticity value of the breast based on the force-height curve. Therein, the processing unit is adapted for optimizing a parameter of the X-ray imaging system based on the determined elasticity value.

The method and the system for optimizing X-ray imaging during a mammographic examination may be employed with 2-dimensional mammography and with X-ray tomosynthesis.

It has to be noted that features described with respect to the method for optimizing X-ray imaging during a mammographic examination as described above and in the following may be features of the system and vice versa.

These and other aspects of the invention will be apparent from and elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
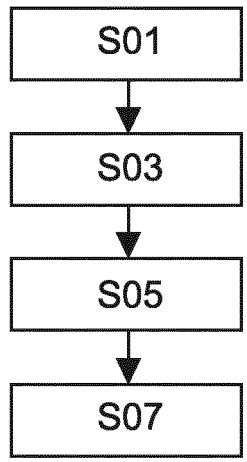
FIG. 1 schematically shows basic steps of a method for optimizing X-ray imaging during a mammographic examination according to an embodiment of the invention FIG. 2 schematically shows a further embodiment of a method according to the invention

In FIG. 1 a flow chart of a method for optimizing X-ray imaging during a mammographic examination is shown schematically. The details and components of the corresponding system 1 are described with respect to FIG. 7. Therein, in a first step S01 a breast 7 is compressed between a support plate 5 and a compression plate 3. In step S03 a force-height curve 13 is acquired during compression. Furthermore, in step S05 an elasticity value, particularly a stiffness, an elasticity or a glandularity of the breast 7 is determined in a radiation-free manner, based on the force-height curve 13. Subsequently, in step S07 a parameter of an X-ray imaging system 1 is optimized based on the determined stiffness, elasticity or glandularity.

In other words, the method provides a radiation-free possibility to predict or estimate the glandularity of a breast 7 under examination. The prediction is based on breast stiffness which is measured prior to the X-ray scan. For this purpose the breast 7 is positioned between a compression plate 3, also denoted as compression paddle, and a support plate 5. The force-height curve 13, also denoted as compression curve, may be acquired for example with the help of sensors such as force sensors and distance sensors. Therein, a breast height L which is dynamic, i.e. varies over time during the compression, is determined. Furthermore, the compression force F which depends on the compressed breast height L and other influencing factors and which is also dynamic, i.e. varies over time, is determined.

In the following embodiments the glandularity is determined as elasticity value. However, the parameters of the X-ray imaging system 21 may also be optimized based on an elasticity or on a stiffness of the breast.

The glandularity for the breast 7 under examination is determined based on the force-height curve 13 and thus radiation-free. Particularly, the glandularity is calculated based on the elasto-mechanical properties, e.g. on the elasticity, of the breast 7. Based on the determined glandularity at least one parameter of the X-ray imaging system 1, i.e. of the X-ray acquisition protocol during the mammographic examination, is adjusted or optimized.

An estimate of breast glandularity prior to X-ray imaging is beneficial for choosing optimal and individual scan parameters, because glandularity influences the x-ray attenuation of an X-ray examination. A further advantage of the method as described above is that additional dose for the patient and the medical personal may be avoided because the glandularity is determined radiation-free and thus no pre-scan is necessary. Moreover, based on the determined glandularity the pressure on the breast 7, i.e. the compression force, and/or the scan duration may be adjusted. In cases where the density, i.e. the glandularity of the breast is very high an output signal may even suggest other adequate examination procedures such MRI or ultrasound.

Figure 2:
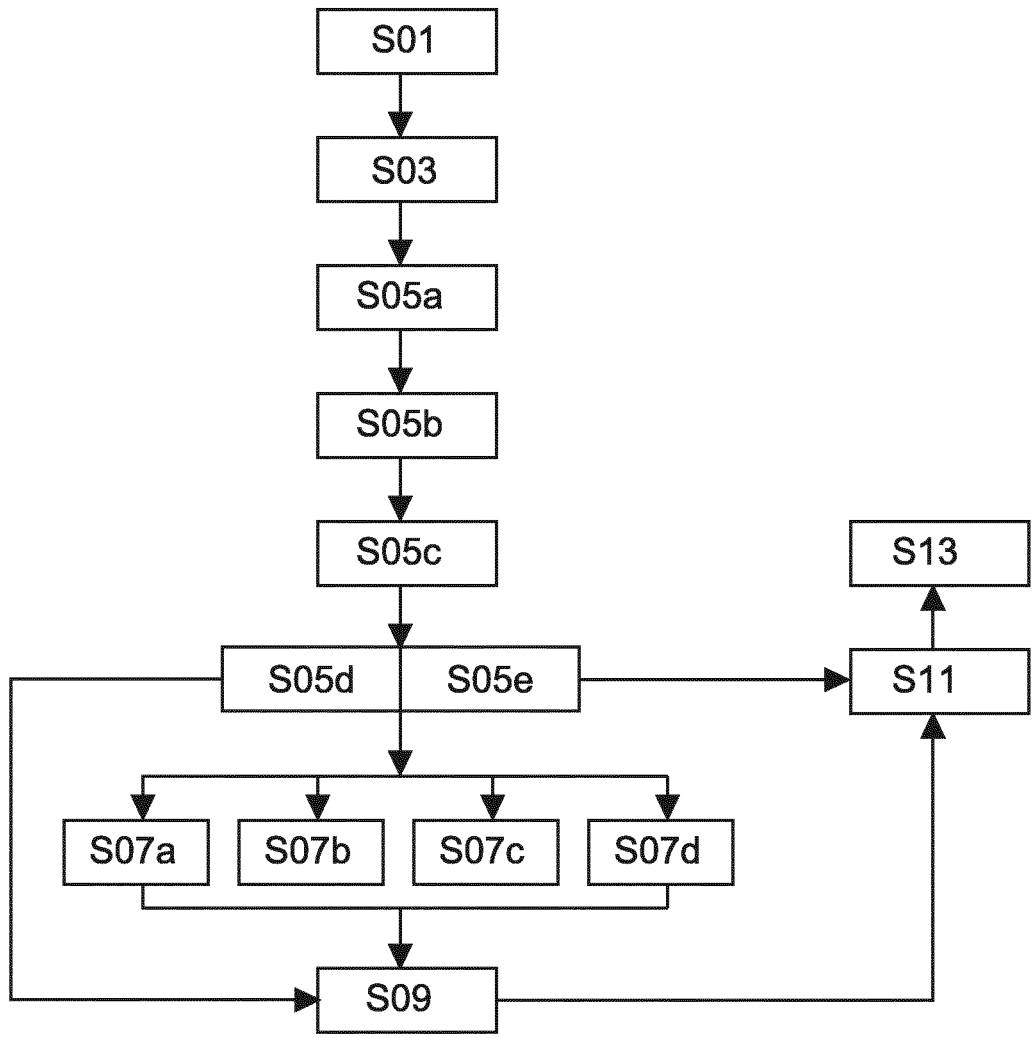

FIG. 2 shows a flow chart according to a further exemplary embodiment of the method. Steps S01 and S03 are similar or identical to the first two steps shown in FIG. 1. However, step S05 is divided, i.e. comprises further steps S05a to S05e. In other words determining the glandularity of the breast 7 comprises further steps.

In step S05a a breast contact area A between the breast 7 under examination and a compression plate 3 or a support plate 5 is determined. I.e. the breast contact area A may be seen as the area of the breast which is in direct contact, i.e. flat on the compression plate 3 or the support plate 5. Particularly, the breast contact area A may be determined automatically, e.g. with a camera and visual markers 45 on at least one of the compression plate 3 and the support plate 5. The visual markers 45 may be integrated into the plates 3, 5 or may be projected onto the plates 3, 5 by a projector 43 (FIG. 7) such as for example by a laser. E.g. the breast contact area A may be determined automatically by a camera with the help of an algorithm which compares the imaged breast area A with breast sizes shown on the compression plate 3. Alternatively, the breast contact area A may be determined manually i.e. visually by a user. For example, a user may visually categorize the breast 7 under examination as size A, B, C, . . . . Moreover, the breast contact area A may be measured directly or indirectly. An indirect measurement of the breast contact area A may comprise determining a length of the breast from the chest wall to the mammilla and relating the determined length to an area e.g. via a regression curve. Advantageously, the breast contact area A is determined at the end of the compression process.

In a further optional step S05$b$ the breast height L is determined at the end of the compression process. Alternatively, the breast height L at the end of the compression process may be derived from the acquired force-height curve 13. Therein, the breast height L, i.e. the overall breast height L is the sum of the average height $L_g$ of glandular tissue and of the average height $L_f$ of fatty tissue: $L=L_g+L_f$.

Moreover, in step S05$c$ a stiffness $k=\Delta F/\Delta L$, also denoted as modulus of resilience or spring constant, is determined based on the force-height curve 13. For example, the stiffness may be derived from the slope of the force-height curve 13 at the end of the compression process. It may be advantageous to derive the stiffness of the breast 7 at the end of the compression process where the force-height curve is mostly linear and the deformation of the breast 7 is mainly elastic. This effect may be due to less blood outflow and thus less relaxation effects in the breast 7. Therefore, if the stiffness is determined at the end of the compression process the reliability of the stiffness measurement may be improved, i.e. less variations in the elastic module may be detected. Alternatively, the elasto-mechanical model may also be more complex and involve also viscosity terms which may allow using parts of the compression curve other than the final part.

In step S05$d$ a set of equations is employed to determine the glandularity. The determination of the glandularity based on the set of equations is explained with respect to FIG. 3 to FIG. 5 below. Alternatively or additionally, the acquired force-height curve 13 is compared with a database of measured values to determine the glandularity in step S05$e$. Therein, the database of measured values may be used as a look-up table or for a curve fit of the force-height curve 13.

Therein, according to a further exemplary embodiment of the invention, the glandularity may be determined automatically. I.e. the glandularity may be determined automatically by the system 1, e.g. by a processing unit 37, without user interaction.

After determining the glandularity in step S05 and particularly in step S05$d$ and/or in step S05$e$, a first output signal 27 representative of the glandularity may be generated in step S09. The first output signal 27 may be an optical and/or an acoustical signal. For example, the first output signal 27 may be provided as a digital number or as a classification symbol of breast densities. The first output signal 27 may be provided on one or several displays 25 and may for example be utilized by a user to make a first estimation of the required pressure force and of further system parameters.

Before generating the first output signal 27 or in parallel to generating the first output signal 27, one or several parameters of the X-ray imaging system 1 are optimized based on the determined glandularity in step S07. Particularly, in step S07$a$ a tube anode voltage, e.g. the maximum tube anode voltage (KVP) of an X-ray source 15 may be optimized based on the determined glandularity. Additionally or alternatively, a tube current of the X-ray source 15 may be optimized based on the determined glandularity. Therein, the tube current represents the value in mA with which the electrons are accelerated within the tube of the X-ray source 15. Additionally or alternatively, an X-ray exposure time may be optimized based on the determined glandularity. Additionally or alternatively, at least one X-ray detector 17 energy threshold value may be optimized based on the determined glandularity. Additionally or alternatively, an X-ray pre-filter property such as material or pre-filter thickness may be optimized based on the determined glandularity.

The anode voltage determines the energy of the electrons of the X-ray source 15. Thus, the individual adjustment or optimization of a maximum anode voltage of the X-ray source 15 may reduce or increase the energy deposition within the breast during the X-ray scan in such a way that the signal to noise ratio and/or the image contrast are enhanced and the dose to the patient possibly reduced while the examination time is possibly optimized.

The X-ray detector energy threshold value may be particularly advantageously optimized, especially for spectral detectors. Particularly, when using two energy bins in a photon-counting detector 17, the threshold between the low and the high energy bin may be chosen such that the expected counts in both bins become approximately equal. This helps in optimizing spectral sensitivity of the X-ray detector 17.

An X-ray pre-filter material or pre-filter thickness may be adjusted on a patient-dependent basis, e.g. choosing a harder pre-filtering can remove low-energy components of the tube X-ray spectrum which would be mainly absorbed in denser breasts and hence not contribute to the signal but only to the X-ray dose.

After determining the glandularity in step S05 and particularly in step S05$d$ and/or in step S05$e$, a compression force limit based on at least one of the following quantities may be determined in step S11: the breast contact area A, the stiffness of the breast 7 and the glandularity of the breast 7. Therein, step S11 may be executed before, after or in parallel to steps S07$a$ to S07$e$ and/or step S09.

After determining the compression force limit in step S011 a second output signal 29 representative of the relation between the quantity and the compression force limit is provided, when the compression force limit is reached during the mammographic examination. Similarly to the first output signal 27, the second output signal 29 may be an optical and/or an acoustical signal. For example, the second output signal 29 may be provided on one or several displays 25. Particularly, the second output signal 29 may be provided on the same or on a different display 25 as the first output signal 27.

According to an exemplary embodiment of the invention, the second output signal 29 may indicate on a display 25 whether the applied compression force is low, ok or high for the determined breast contact area and/or glandularity. According to a further exemplary embodiment, the second output signal 29 may indicate on a display 25 for which glandularity the currently applied force is ok.

Based on the values determined in steps S03 and S05$a$ to S05$c$ the glandularity of the breast 7 under examination may be determined as described below with reference to FIG. 3 to FIG. 5.

Figure 3:
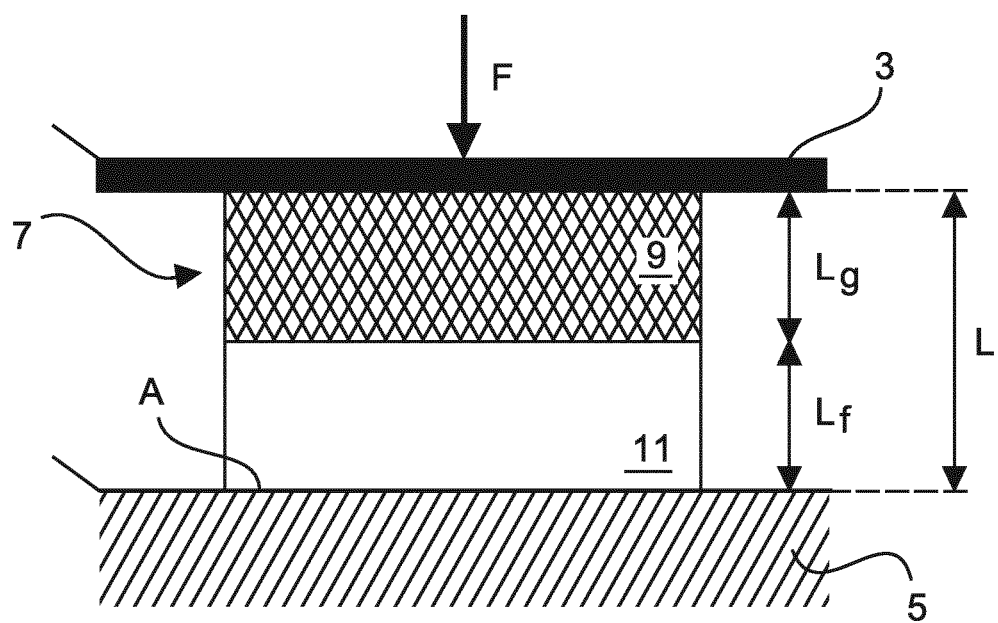
FIG. 3 shows a mechanical two-component model of a compressed breast

In FIG. 3 a mechanical two-component model of a compressed breast 7 is shown on which the calculation of the glandularity may be based. The shown female breast 7 is mostly composed of two tissue types: glandular tissue 9 and fatty tissue 11. The breast 7 in FIG. 3 is positioned between a compression plate 3 and a support plate 5. A force F is exerted onto the breast 7 by the compression plate 3 and/or the support plate 5. The area on the support plate 5 denoted by A represents the breast contact area. As mentioned above the breast height L, i.e. the overall breast height L is the sum of the average height $L_g$ of glandular tissue 9 and of the average height $L_f$ of fatty tissue 11:

$$L = L_g + L_f$$

The stiffness of the breast 7 may be denoted as follows:

$$k = \frac{\Delta F}{\Delta L} \quad (1)$$

The average elastic modulus, also denoted as Young's modulus of the breast 7, may be determined or estimated as follows:

$$E_{ave} = \frac{L}{A} \cdot \frac{\Delta F}{\Delta L} \quad (2)$$

The stiffness or spring constant of the glandular tissue 9 in FIG. 1 may be calculated as $$k_f = E_f \cdot \frac{A}{L_f} \quad (3)$$

The stiffness or spring constant of the fatty tissue 11 in FIG. 1 may be calculated as $$k_g = E_g \cdot \frac{A}{L_g} \quad (4)$$

The two tissue components, i.e. the glandular tissue 9 and the fatty tissue 11, are subject to the same force F in series as shown in FIG. 3. Thus, the overall stiffness or spring constant is:

$$k_{ave} = \frac{1}{k_f^{-1} + k_g^{-1}} = E_{ave} \frac{A}{L_f + L_g} \quad (5)$$

This is equivalent to:

$$\frac{L_f}{L_g} = \frac{E_{ave} \cdot E_f - E_g \cdot E_f}{E_g \cdot E_f - E_{ave} \cdot E_g} \quad (6)$$

Therein, glandularity may be defined as $$g = \frac{L_g}{L_g + L_f} \quad (7)$$

When equations (6) and (7) are combined the following equation is obtained for glandularity:

$$g = \frac{1 - E_f/E_{ave}}{1 - E_f/E_g} \quad (8)$$

In the equations above F corresponds to the measured force excreted on the breast 7 during compression, L corresponds to the measured compression height, $k = \Delta F/\Delta L$ corresponds to the stiffness or modulus of resilience, A corresponds to the breast contact area between the breast 7 and the support plate 5 or the compression plate 3.

If a measured elastic modulus $E_{ave}$ of a breast 7 under examination is equal to the elastic modulus $E_f$ of fatty tissue 11, the glandularity value corresponds to zero, i.e. g=0. Furthermore, if the elastic modulus $E_f$ of fatty tissue 11 equals the elastic modulus $E_g$ of glandular tissue 9, the glandularity value corresponds to one, i.e. g=1.

The average elastic modulus $E_{ave}$ as shown in equation (2) may be determined from measurements of the breast height L, the breast contact area A and the stiffness k of the breast 7. The measurements of breast contact area A are explained in more detail with respect to FIG. 6. Furthermore, the determination of the stiffness k is described in more detail with respect to FIGS. 4 and 5.

Moreover, the elastic moduli $E_g$ and $E_f$ of glandular tissue 9 and fatty tissue 11 respectively, may be obtained e.g. from scientific literature or e.g. from an experimental database. Thus, after determining the average elastic modulus $E_{ave}$ the glandularity of the breast 7 may be calculated according to equation (8).

Figure 4:
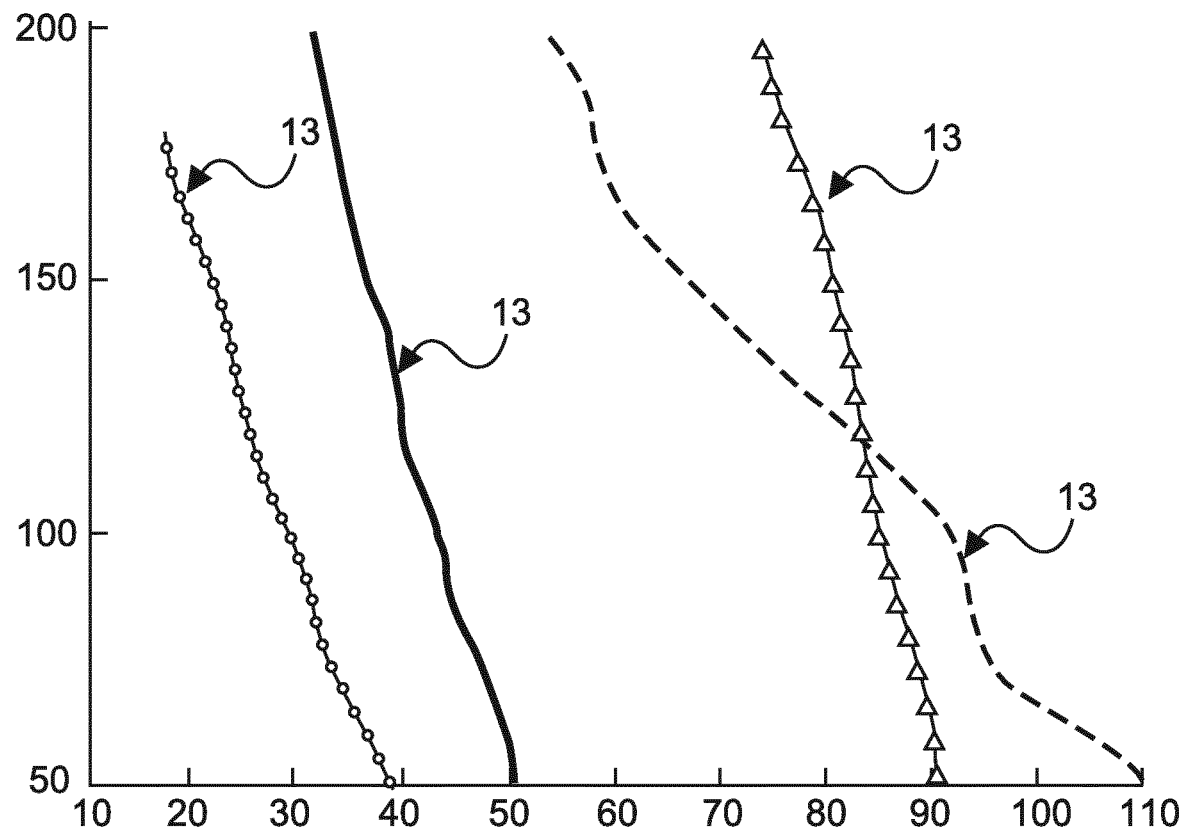
FIG. 4 shows a graph representing examples of force-height curves of different breast phantoms

In FIG. 4, examples of force-height curves 13 of different breast phantoms are shown. These force-height curves 13 may be used to determine the stiffness of the breast 7. On the x-axis the height L of the breast 7 is shown in mm. On the y-axis the compression force is shown in N. Therein, breast phantoms are artificial models of a human female breast. The solid line and the line with circles represent force-height curves 13 of breast phantoms comprising tissue equivalent materials (CIRS), i.e. these phantoms have a physical consistency similar to human tissue. The solid line represents a force-height curve 13 of a breast phantom with a stiffness of k=10.0 N/mm. The line with circles represents a force-height curve 13 of a breast phantom with a stiffness of k=6.3 N/mm.

Moreover, the dashed line and the line with triangles represent force-height curves 13 of breast phantoms comprising foam plastic. The dashed line represents a force-height curve 13 of a breast phantom with a stiffness of k=8.7 N/mm. The line with triangles represents a force-height curve 13 of a breast phantom with a stiffness of k=2.5 N/mm. As may be seen from FIG. 4 the overall stiffness of a breast 7 is correlated to the slope of the force-height curve 13 and thus may be derived from the force-height curve 13.

However, the model shown in FIG. 3 and the breast phantoms used to acquire the force-height curves 13 in FIG. 4 are simplified elasto-mechanical models of the breasts. A real human breast may exhibit a non-linear behavior. Therein, the modulus of resilience may vary depending on the compression force.

Figure 5:
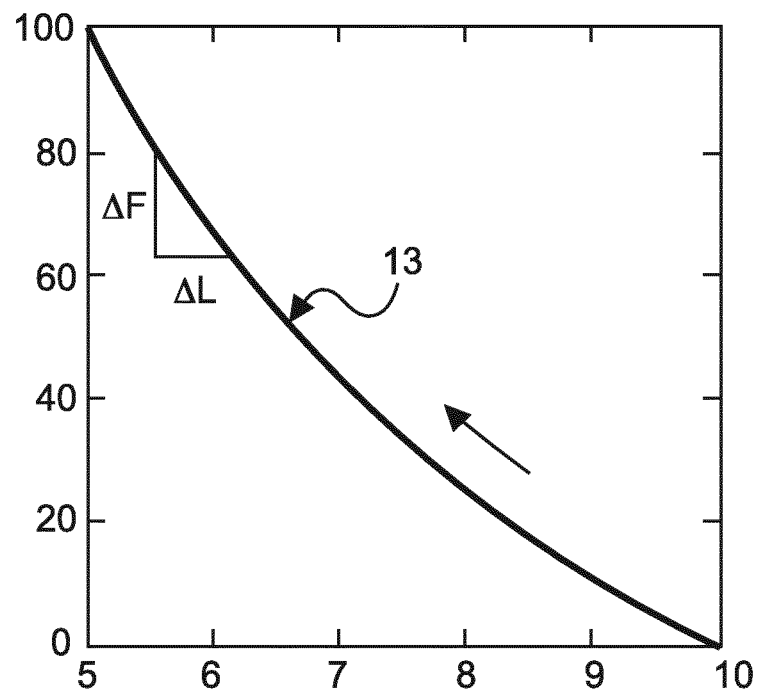
FIG. 5 shows a graph of a force-height curve of a human breast

In FIG. 5 a force-height curve 13 of a more realistic breast model as compared to FIG. 4 is shown. Therein, the x-axis shows the height L of the breast 7 in mm and the y-axis shows the compression force in N. In the model used for FIG. 5 the variation of the stiffness k of the breast 7 depending on the compression force is taken into account. Additionally, the dependency of the force-height curve 13 on relaxation effects due to blood outflow and the viscoelastic deformation of the breast 7 are taken into account. The force-height curve 13 tends to be more linear at the end of the compression process than e.g. in the beginning or in the first part of the compression process. Therein, the end of the compression process may denote 1 to 2 mm of change of the breast height L before the compression is stopped.

As the effects mentioned above are less pronounced at the end of the compression process, the measurement or estimation of the stiffness k carried out at the end of the compression process may help in improving the reliability of the measurement. An additional or alternative possibility for improving the determination of the glandularity may be a database of measured values. Such a database may be used as a look-up-table or for a curve fit.

Figure 6:
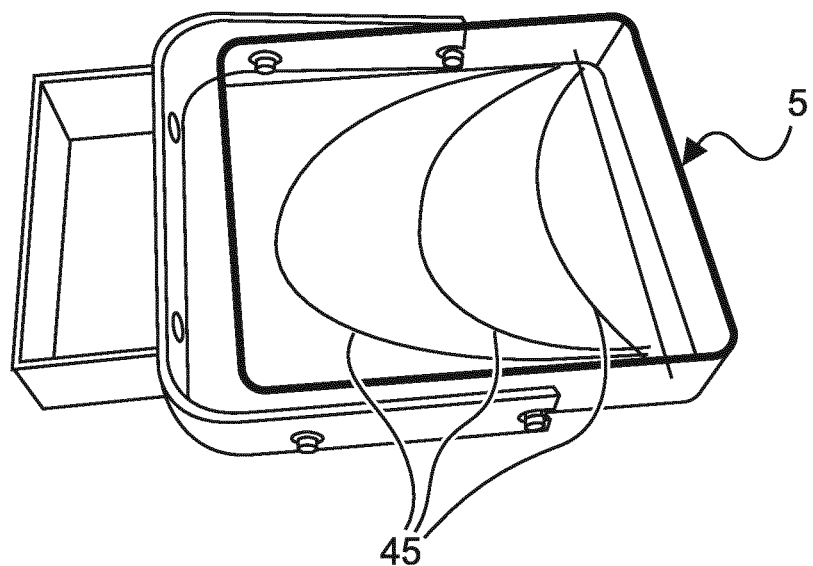
FIG. 6 shows a support plate with markers for determining a breast contact area

In FIG. 6, a support plate 5 with visual markers 45 for determining a breast contact area A is shown. A compression plate 3 may be designed similarly with visual markers 45. The breast contact area A is required for determining $E_{ave}$ according to equation (2). The value of the breast contact area A may be estimated visually by a user or operator. The support plate 5 or a similar compression plate 3 may help in determining the breast contact area A. Therein, the visual markers 45 may be integrated into the palate 3, 5 or alternatively be projected onto the plate 3, 5 e.g. by laser light. In this scenario, an input device such as a range of buttons might be available directly at or close to the breast support to allow the operator to commit or provide this information to the system. Alternatively or additionally, a camera, particularly a small camera may be used to automatically detect and measure the breast contact area. Therein, the breast contact area is easier to determine than the glandularity itself.

Figure 7:
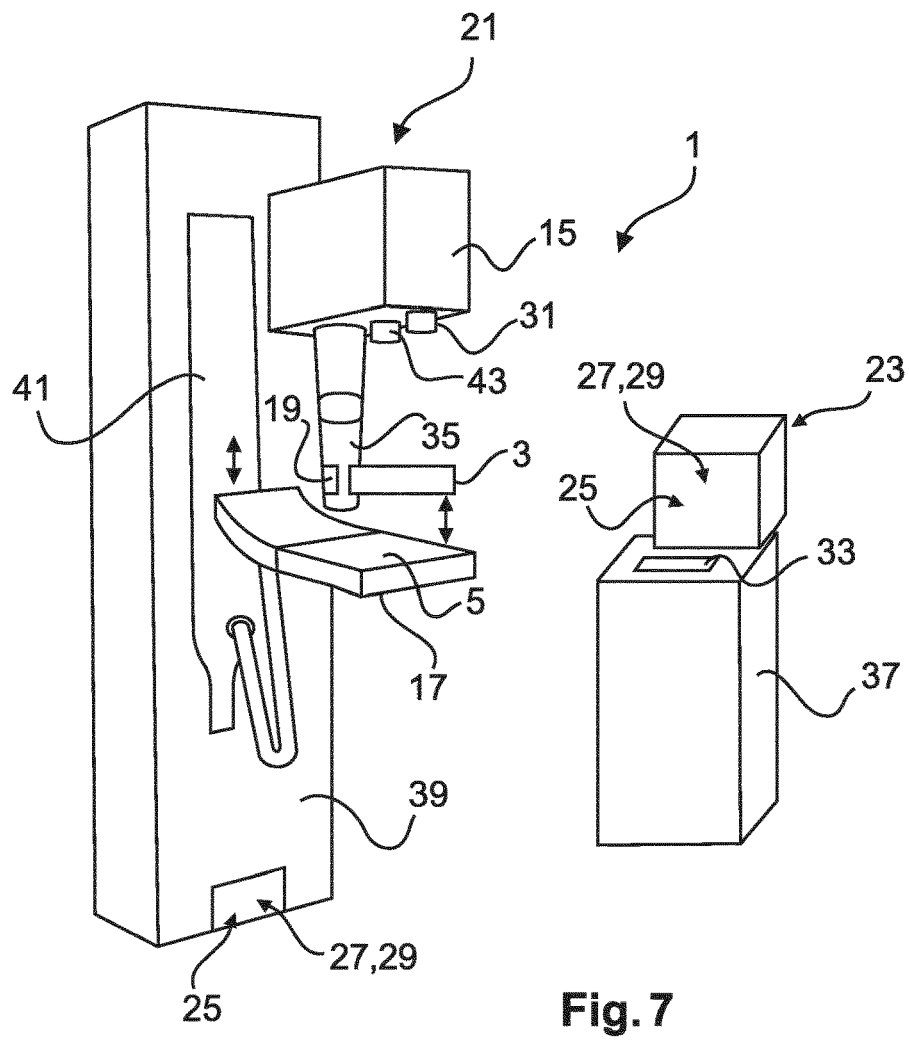
FIG. 7 shows a system for optimized X-ray imaging during a mammographic examination according to an embodiment of the invention

FIG. 7 schematically shows a system 1 for optimized X-ray imaging during a mammographic examination according to an embodiment of the invention. The system 1 comprises a support plate 5 for supporting a breast 7 while radiographic images are obtained. Furthermore, the system comprises a compression plate 3 for compressing the breast 7 between the support plate 5 and the compression plate 3 while the radiographic images are obtained. One of the compression plate 3 and the support plate 5 may be designed movable with relation to the other plate. A breast 7 under examination may be positioned between the support plate 5 and the compression plate 3 such that the support plate 5 is below and the compression plate 3 above the breast 7. The compression plate 3 and the support plate 5 are part of an X-ray imaging system 21, also denoted as an apparatus for mammographic examinations.

The system 1 furthermore comprises a monitoring unit 23 which may be part of a processing unit 37. The monitoring unit 23 may be connected wirelessly or by cables to several components of the system 1 (not shown in FIG. 7). For example, monitoring unit 23 may be connected to a screen or display 25, to an interaction device 33 also denoted as interface unit, to a tracking device 31, to an X-ray source 15, to an X-ray detector 17, to a force sensor 19, to a compressing device 35, to an adjustable support 41 and to a projector 43.

The monitoring unit 23 is adapted for acquiring a force-height curve 13 during compressing of the breast 7. Particularly, the monitoring unit 23 may be adapted for acquiring over a certain time the measurements of a force sensor 19 or of a pressure sensor. Furthermore, the monitoring unit 23 may be adapted to automatically determine a breast contact area A between the breast 7 and the compression plate 3 or between the breast 7 and the support plate 5. Moreover, the monitoring device 23 may be adapted for deriving a stiffness of the breast 7 under examination from the force-height curve 13.

Furthermore, the monitoring device 23 may be adapted for determining a compression force limit based on the determined breast contact area A, on the stiffness of the breast or on the glandularity of the breast. Therein, the monitoring device 23 may transmit the acquired and determined values to the processing unit 31.

The processing unit 37 is adapted to determine, in a radiation-free manner, the glandularity of the breast 7 based on the force-height curve 13. For this purpose a database of measured values and/or a corresponding algorithm may be stored at the processing unit 37. Furthermore, the processing unit 37 is adapted for optimizing a parameter of the X-ray imaging system 21 based on the determined glandularity. The parameters to be optimized are described above.

System 1 and particularly the X-ray imaging system 21 is adapted for acquiring radiographic images of the breast 7. The imaging system comprises an X-ray source 15 and an X-ray detector 17. The example shown in FIG. 7 is a so-called stand-up investigation system where, for example, a patient in an upright position can stand while, for example, the breast is examined.

Therefore, the X-ray detector 17 is provided as a sort of a paddle or small table upon which a breast 7 can be received. Thus, the X-ray detector 17 may be positioned under the support plate 5 or be integrated into the support plate 5. The moveable compression plate 3 is provided with an adaptable distance to the X-ray detector 17 in order to be able to act with a desired pressing force on the breast. The compression plate 3 is attached to a compressing device 35 allowing the necessary movement of the compression plate 3.

The X-ray source 15 generates X-ray radiation emanating towards the X-ray detector 17. Therefore, the compression plate 3 is designed as X-ray transparent. The X-ray source 15 and the X-ray detector 17 are attached to an adjustable support 41 allowing for a vertical adjustment such that the height of the X-ray detector 17 may be adapted to different sizes of the person under examination. A rotational movement of the imaging system is possible to acquire X-ray images not only in a vertical direction, but also in a direction with an angle to the vertical direction, such as for example 30° or an X-ray viewing direction in a horizontal way. Imaging may take place at a single, fixed orientation, for conventional mammography, but also alternatively at a range of multiple angular positions for tomosynthesis acquisitions. A base 39 is provided which is for example securely fixed to a floor of an examination room.

According to a further embodiment of the invention the system 1 further comprises a display 25 adapted for displaying the first and/or the second output signals. The display 25 may include optical and acoustical means. Furthermore, the display 25 may be provided as a separate device and/or for example be included into the base 39 of the system 1. Moreover, several displays 25 may be provided as shown in FIG. 7. The displays 25 may be connected to a processing unit 37, and in particular to the monitoring device 23. Moreover, the display 25 may be connected to an interaction device 33 such as a keyboard. Alternatively, the display 25 may include the interaction device 33 for example in form of a touch screen. The interaction device 33 may serve for example for a manual input of the breast contact area A into the monitoring device 23.

It must be noted that the X-ray imaging system shown is a so-called stand type. It is further noted that the present invention also comprises other types for X-ray imaging, for example moveable or stationary X-ray imaging systems or X-ray imaging systems with a table upon which a patient can be received in order to acquire X-ray images while the patient is lying on the table, for example facing downwards.

According to a further embodiment of the invention the system 1 comprises a tracking device 31 for measuring the breast contact area A in real time. For example, the tracking device 31 may be arranged above the breast 7 and above the compression plate 3. The tracking device 31 may be a system of optical cameras which acquire the breast contact area A for example in combination with visual markers 45 as described in the embodiment of FIG. 6. The measured breast contact area value may be provided by the tracking device 31 to the monitoring device 23 where a stiffness of the breast is determined or directly to the processing unit 37.

According to a further embodiment of the invention the system 7 comprises a force sensor 19 which measures the currently applied compression force and provides the measured values to the monitoring device 23.

Figure 8:
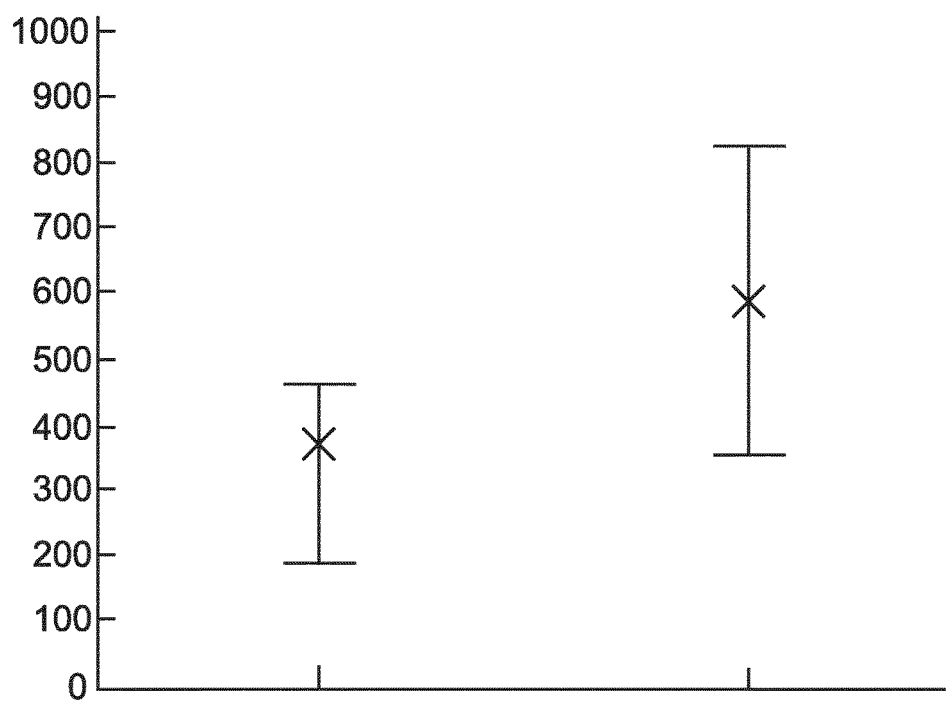
FIG. 8 shows a graph representing a calculated modulus of elasticity for different breasts

In FIG. 8 a representation of a calculated modulus of elasticity for different groups of breasts is shown. The graph in FIG. 8 is based on a study with 12 women. For each woman a dynamic force-height curve 13 was recorded. Furthermore, an experienced radiography assistant estimated the (BIRADS) breast density by palpation. Six of the study participants were estimated as BIRADS density 2, which corresponds to scattered fibroglandular breasts and six of the participants were estimated as BIRADS density 3, which corresponds to heterogeneously dense breasts.

From the acquired force-height curves 13 the modulus of elasticity was determined according to equation (2). Here the stiffness k was derived as the slope at the end of the compression progress, where the deformation is mainly elastic. The height L of the breast 7 was measured as the compression height at the end of the compression process and the breast contact area A was estimated from the breast length, i.e. the length of the breast from the chest wall to the mammilla at the end of the compression process. These values were inserted into equation (2). The results are shown in FIG. 8.

Therein, the left part of FIG. 9 represents the modulus of elasticity $E_{ave}$ of a group of scattered fibroglandular breasts and the right part of FIG. 8 represents the modulus of elasticity $E_{ave}$ for a group of heterogeneously dense breasts. On the y-axis the calculated modulus of elasticity is shown in $N/m^2$. The cross represents the mean value of the modulus of elasticity for each group respectively. The bars represent the minimum and maximum values of the modulus of elasticity for each group respectively.

FIG. 8 shows the practical feasibility of determining the modulus of elasticity $E_{ave}$ and thus also of determining the glandularity from the force-height curves 13. A statistically significant difference in the modulus of elasticity $E_{ave}$ is detectable in FIG. 8 between the two groups of breasts with different density.

According to a further embodiment of the invention a computer program or a computer program element is provided that is characterized by being adapted to execute the method steps of the method according to one of the preceding embodiments, on an appropriate system.

The computer program element might therefore be stored on a computing unit, which might also be part of an embodiment of the invention. This computing unit may be adapted to perform or induce a performing of the steps of the method described above. Moreover, it may be adapted to operate the components of the above described system or apparatus. The computing unit can be adapted to operate automatically and/or to execute the orders of a user. A computer program may be loaded into a working memory of a data processor. The data processor may thus be equipped to carry out the method of the invention.

This embodiment of the invention covers both, a computer program that right from the beginning uses the invention and a computer program that by means of an up-date turns an existing program into a program that uses the invention.

Furthermore, the computer program element may be adapted for providing all necessary steps to fulfil the procedure of an exemplary embodiment of the method as described above.

According to a further embodiment of the invention a computer readable medium, such as a CD-ROM, is presented wherein the computer readable medium has a computer program element stored on it which computer program element is described by the preceding section.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device or system type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

LIST OF REFERENCE SIGNS 1 system
3 compression plate
5 support plate
7 breast
9 glandular tissue
11 fatty tissue
13 force-height curve
15 X-ray source
17 X-ray detector
19 force sensor
21 X-ray imaging system (apparatus for mammographic examination)

23 monitoring unit
25 display
27 first output signal
29 second output signal
31 tracking device (optical cameras)
33 interaction device (interface unit)
35 compressing device
37 processing unit
39 base
41 adjustable support
43 projector
45 visual markers
F compression force exerted on a breast
A breast contact area
L height of a breast
$L_g$ height of glandular tissue
$L_f$ height of fatty tissue
k stiffness of the breast
g glandularity
S01 compressing a breast between a support plate and a compression plate
S03 acquiring a force-height curve during compressing
S05 radiation-free determining of a glandularity of the breast based on the force-height curve
S05a determining a breast contact area between a breast under examination and a compression plate or a support plate
S05b determining a breast height at the end of the compression process
S05c determining a stiffness of the breast based on the force-height curve
S05d using a set of equations to determine the glandularity
S05e comparing the acquired force-height curve with a database of measured values to determine the glandularity
S07 optimizing a parameter of an X-ray imaging system based on the determined glandularity
S07a optimizing a tube anode voltage of an X-ray source based on the determined glandularity
S07b optimizing a tube current of the X-ray source based on the determined glandularity
S07c optimizing an X-ray exposure time based on the determined glandularity
S07d optimizing an X-ray detector energy threshold value based on the determined glandularity
S09 providing a first output signal representative of the glandularity
S11 determining a compression force limit based on at least one of the following parameters: the breast contact area, the stiffness of the breast and the glandularity of the breast
S13 providing a second output signal representative of the relation between the parameter and the compression force limit, when the compression force limit is reached during the mammographic examination

The invention claimed is:

1. A method for optimizing an X-ray imaging system during a mammographic examination, comprising:
    compressing a breast between a support plate and a compression plate;
    acquiring a force-height curve during compressing;
    determining an elasticity value of the breast by:
        determining a breast contact area between the breast and the compression plate or the support plate; and
        determining a stiffness of the breast based on the force-height curve; and
    optimizing a parameter of the X-ray imaging system based on the determined elasticity value.

2. The method according to claim 1, wherein the optimized parameter is at least one of: a tube anode voltage of an X-ray source, a tube current of the X-ray source, an X-ray pre-filter property, an X-ray exposure time, and an X-ray detector energy threshold value.

3. The method according to claim 1, wherein determining the stiffness of the breast is implemented at the end of compressing.

4. The method according to claim 1, further comprising providing a first output signal representative of the elasticity value.

5. The method according to claim 4, wherein the first output signal is at least one of an optical signal and an acoustical signal.

6. The method according to claim 1, further comprising
    determining a compression force limit based on at least one of: the breast contact area, the stiffness of the breast, and a glandularity value of the breast;
    providing a second output signal representative of a relation between a quantity and the compression force limit;
    wherein the second output signal is provided when the compression force limit is reached during the mammographic examination.

7. An X-ray imaging system for optimizing X-ray imaging during a mammographic examination, comprising:
    an X-ray imaging system for acquiring radiographic images of the breast;
    a support plate for supporting a breast while the radiographic images are obtained;
    a compression plate for compressing the breast between the support plate and the compression plate while the radiographic images are obtained;
    a monitoring unit for acquiring a force-height curve during compressing;
    a processor for determining an elasticity value of the breast by:
        determining a breast contact area between the breast and the compression plate or the support plate; and
        determining a stiffness of the breast based on the force-height curve;
    wherein the processor is configured for optimizing a parameter of the X-ray imaging system based on the determined elasticity value.

8. The system according to claim 7, wherein the optimized parameter is at least one of: a tube anode voltage of an X-ray source, a tube current of the X-ray source, an X-ray pre-filter, an X-ray exposure time, and an X-ray detector energy threshold value.

9. A computer program element for controlling an X-ray imaging system, wherein, when the program element is executed by a processor, the system is configured to perform a method for optimizing the X-ray imaging system during a mammographic examination, the method comprising:
    compressing a breast between a support plate and a compression plate;
    acquiring a force-height curve during compressing;
    determining an elasticity value of the breast by:
        determining a breast contact area between the breast and the compression plate or the support plate; and
        determining a stiffness of the breast based on the force-height curve; and
    optimizing a parameter of the X-ray imaging system based on the determined elasticity value.

10. A non-transitory computer readable medium having one or more executable instructions stored thereon, which when executed by a processor, cause the processor to perform a method for optimizing an X-ray imaging system during a mammographic examination, the method comprising:
   compressing a breast between a support plate and a compression plate;
   acquiring a force-height curve during compressing;
   determining an elasticity value of the breast by:
      determining a breast contact area between the breast and the compression plate or the support plate; and
      determining a stiffness of the breast based on the force-height curve; and
   optimizing a parameter of the X-ray imaging system based on the determined elasticity value.

11. The method according to claim 1, further comprising determining a glandularity value of the breast based on the determined elasticity value.

* * * * *